(12) United States Patent
Akashi

(10) Patent No.: US 6,286,955 B1
(45) Date of Patent: Sep. 11, 2001

(54) BIOCOMPATIBLE LENS, AND METHOD OF PRODUCING THE SAME

(75) Inventor: Mitsuru Akashi, Kagoshima (JP)

(73) Assignee: Tetsuya Sakai, Yamaguchi-ken (JP)

( * ) Notice: Subject to any disclaimer, the term of this patent is extended or adjusted under 35 U.S.C. 154(b) by 0 days.

(21) Appl. No.: 09/461,295

(22) Filed: Dec. 15, 1999

(51) Int. Cl.[7] ................................. G02C 7/04; A61F 2/16
(52) U.S. Cl. ..................... 351/160 H; 351/177; 623/6.62
(58) Field of Search .......................... 351/160 H, 160 R, 351/161, 162, 177; 623/6.62

(56) References Cited

U.S. PATENT DOCUMENTS

| | | | |
|---|---|---|---|
| 3,876,581 | * | 4/1975 | Neogi ................................. 260/901 |
| 4,028,295 | * | 6/1977 | Loshaek ............................ 351/160 H |
| 5,674,283 | * | 10/1997 | Stoy .......................................... 623/6 |

* cited by examiner

*Primary Examiner*—Scott J. Sugarman
(74) *Attorney, Agent, or Firm*—Smith, Gambrell & Russell, LLP

(57) ABSTRACT

A biocompatible lens used for a contact lens directly contacted to the eyeball via tears or for an artificial crystalline lens, in which alkoxyalkyl (meth)acrylate (co)polymer layer is formed on the surface of the lens. This biocompatible lens is almost free from adhesion of lipid and protens in tears and even if they adhere on its surface, it is possible to wash out them easily.

6 Claims, 1 Drawing Sheet

BIOCOMPATIBLE LENS, AND METHOD OF PRODUCING THE SAME

FIELD OF THE INVENTION

The present invention relates to a biocompatible lens that is almost free from adhesion of lipid and proteins etc. in tears and is easily cleaned by being dipped in a washing liquid; and a method of producing the same.

DESCRIPTION OF THE PRIOR ART

Recently, contact lenses have been widely used for correcting near-sightedness instead of glasses, because wearing of glasses is troublesome. Various materials forming contact lenses have been developed. It is important that the materials hardly get their surface dirty with lipid and proteins in tears or induce allergic response during use of the lens. Therefore, biocompatible polymers are usually used for these materials.

Many concepts concerning the materials of contact lenses has been already disclosed or published. [see, for example, S. Nagaoka et. al., Biomaterials, 11,120, (1990); D. K. Han et.al., J.Biomed.mater.Res., 25,561 (1991); Japanese laid-open (unexamined) patent publication 63-163810, etc.] In these literatures and publications, it is reported that a medical compound containing a hydrophilic group such as a hydroxyl, carbonyl, amide, phosphoric, ether group or the like prevents a contact lens from being stained on its surface by lipid and proteins in tears. It is also reported that materials containing those groups mentioned above are easy to be cleaned and show good biocompatibility.

Furthermore, intraocular lens (artificial crystalline lens) that is implanted instead of an extracted cloudy crystalline lens after completion of the cataract operation has been also developed these days.

SUMMARY OF THE INVENTION

The object of the present invention is to provide a biocompatible lens which comprises materials different from those medical compounds already reported, avoids adhesion of lipid and proteins in tears, is easily cleaned by being dipped in a washing liquid and exhibits biocompatibilities with tissue when implanted; and to provide a method of producing the same.

The inventor of the present invention has assiduously investigated to find a lens-surface modification method which is different from the prior arts and as a result, has found that alkoxyalkyl acrylate or alkoxyalkyl methacrylate polymers or copolymers have excellent properties capable of inhibiting adhesion of lipid and proteins in tears to lens and allowing easy washing out of the lipid and proteins adhered and that the above polymers can be used not only for a contact lens but also for an artificial crystalline lens.

That is, the biocompatible lens of the present invention is used for a contact lens that is contacted directly to the eyeball via tears and for a lens implanted in the eyeball. In the biocompatible lens of the invention, polyalkyl (meth) acrylate containing an alkoxy group or its copolymer is coated on the surface of a lens to exhibit excellent properties. In other words, the surface of the lens is covered with a layer of the coated polyalkyl (meth)acrylate containing an alkoxy group or its copolymer.

In the biocompatible lens of the invention, the layer of polyalkyl (meth)acrylate containing an alkoxy group or its copolymer may be formed onto the surface of the lens by means of graft-copolymerization. In the preparation process of the biocompatible lens of the invention, monomers of the above-mentioned polymers are graft-polymerized, by covalent bonding, with a polymer constituting the non-grafted lens. Therefore, the grafted polymer layer on the surface of the lens can not be easily peeled off and hence, effects such as inhibition of adhesion of lipid and proteins to the surface of the lens and easy washing out of the lipid and proteins adhered or the like can be maintained for a long time.

In the present invention, the alkoxy group introduced to the acrylates is preferably selected from the group consisting of a methoxy group and an ethoxy group.

Further, in the present invention, the above alkoxyalkyl (meth)acrylate (co)polymer is preferably at least one of those polymers such as poly-2-methoxyethyl acrylate, poly-2-methoxyethyl methacrylate, poly-2-ethoxyethyl acrylate, poly-2-ethoxyethyl methacrylate, poly-2-methoxybutyl acrylate and poly-2-methoxybutyl methacrylate.

Polyalkoxyalkyl (meth)acrylate may be a copolymer containing other monomer unit as far as it shows the characteristic properties of polyalkoxyalkyl (meth)acrylate. Examples of the monomers include alkyl (meth)acrylates such as methyl methacrylate, ethyl methacrylate and butyl acrylate, monomers containing nitrogen such as vinyl pyrrolidone, acrylic amide, N,N-dimethyl acrylic amide and isopropyl acrylic amide and monomers containing a reactive group such as glycidyl methacrylate, glycidyl acrylate, acrylic chloride and acryloyloxyethyl isocyanate. These copolymers may be any of random copolymer, graft-copolymer and block copolymer, but it is preferable that the copolymer contains block sequences of alkoxyalkyl (meth) acrylate.

The biocompatible lens of the present invention is produced in the following method comprising three steps. Namely, in the first step, activated radical species is induced on the surface of the lens; in the second step, monomers such as alkoxyalkyl (meth)acrylate or the like are coated onto the surface of the lens and in the third process, the above monomers are polymerized by active radical species generated on the surface of the lens as an initiator. According to the process of the present invention, alkoxyalkyl (meth) acrylate (co)polymers are grafted to the surface of the lens by covalent bonding. Consequently, they are hardly peeled off from the lens surface, compared with conventional polymer coating layers prepared by firstly coating a polymer dissolved in a solvent on a lens surface and then, curing the layer by heat treatment after removal of the solvent. On account of this reason, biocompatible lenses having characteristic properties such as inhibition of lipid and proteins in tears from adhering, easy washing out of lipid and proteins adhered, and long-term maintenance of biocompatibilities can be easily and simply manufactured.

The biocompatible lens of the present invention can be also produced easily and simply by the following method comprising three steps. That is, in the first step, an alkoxyalkyl (meth)acrylate copolymer is dissolved in an organic solvent, then in the second step, the polymer solution thus prepared is coated on the surface of the lens and finally in the third process, the solvent used for dissolving the polymer is removed by vaporization. In the third process, the polymer may be made insoluble by means of heat treatment or addition of additives containing a reactive group for cross linking the polymer. As the solvent, tetrahydrofuran, methylene chloride, chloroform and the like may be used.

Various materials can be used for the biocompatible lens in the present invention. Examples thereof are polymethyl methacrylate, (co)polymers containing silicon or fluorine and (co)polymers containing polyvinyl pyrrolidone, poly-2- hydroxyethyl methacrylate and plyvinyl alcohol as at least one component.

BRIEF DESCRIPTION OF THE DRAWINGS

In FIG. 1, a biocompatible contact lens 1 is contacted directly to the eyeball via tears existing between them when it is used. On the surface S2 of the lens 2, the layer 3 of an alkoxyalkyl (meth)acrylate (co)polymer is formed to inhibit adhesion of lipid and proteins.

PREFERRED EMBODIMENT OF THE INVENTION

Figure 1:
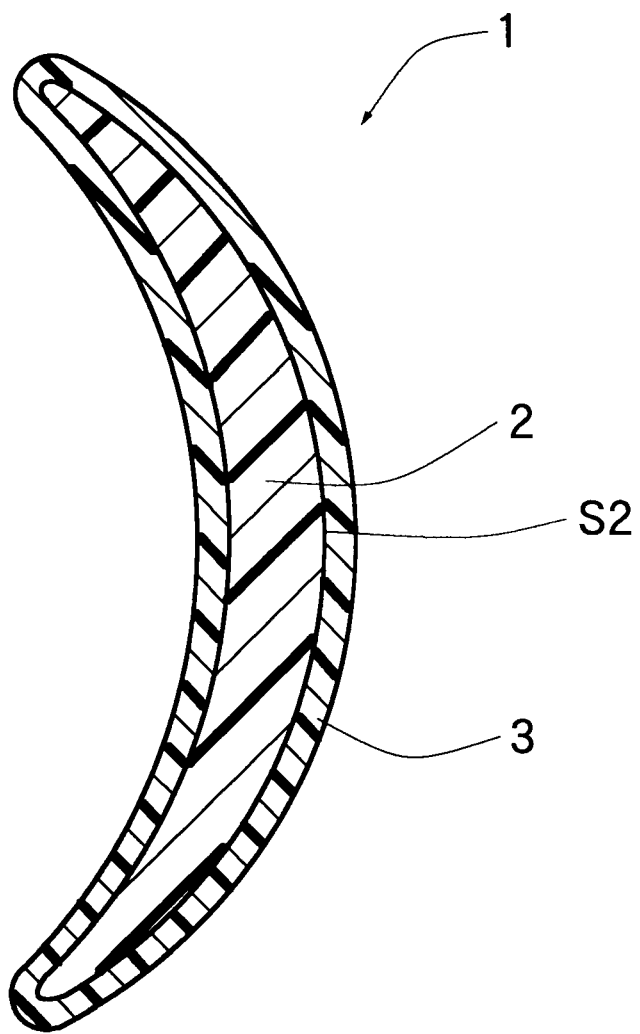
FIG. 1 schematically shows a cross section of a biocompatible contact lens.

In the following Example 1 to 3, a (co)polymer layer inhibiting adhesion of lipid and proteins is formed graft-copolymerization onto the surface (S2) of lens (2).

EXAMPLE 1

A contact lens composed of 45 weight mol % of methacryloxyethoxypropyltris(trimethyl siloxy) silane, 20 weight mol % of hexafluoroisopropylmethacrylate, 20 weight mol % of methyl methacrylate, 8 weight mol % of methacrylic acid and 7 weight mol % of triethylene glycol dimethacrylate was prepared. Then, the contact lens was placed in a reaction vessel, and plasma is generated in an atmosphere of argon to generate radical species on the surface of the contact lens. After reducing the pressure inside the reaction vessel to 0.15 Pa, 2-methoxyethyl acrylate was introduced to carry out graft-copolymerization. After completion of the reaction, unreacted monomer was washed out by Soxhlet extraction, whereby a contact lens having the polymer layer of 2-methoxyethyl acrylate on its surface was obtained.

EXAMPLE 2

A contact lens composed of 98.2 weight mol % of n-butyl acrylate and 1.8 weight mol % of ethylene glycol dimethacrylate was prepared, and its surface was activated with 2-methoxyethyl methacrylate in the same manner as in Example 1.

EXAMPLE 3

A contact lens composed of 74 weight mol % of vinyl pyrrolidone, 25 weight mol % of methyl methacrylate and 1 weight mol % of diallylitaconate was prepared, and its surface was activated in the same manner as in Example 1.

EXAMPLE 4

A contact lens composed of 45 weight mol % of methacryloxyethoxypropyltris(trimethylsiloxy) silane, 20 weight mol % of hexafluoroisopropyl methacrylate, 20 weight mol % of methyl methacrylate, 8 weight mol % of methacrylic acid and 7 weight mol % of triethylene glycol dimethacrylate was prepared. The surface of the obtained contact lens was coated with a copolymer solution consisting of 90 weight mol % of 2-methoxyethyl acrylate and 10 weight mol % of glycidyl methacrylate dissolved in tetrahydrofuran (solvent). Then, the solvent used was vaporized and heat-cured to make the coated copolymer insoluble. In this way, a biocompatible lens having a surface activated by the above copolymer was obtained.

Contact lenses not having biocompatible surface were prepared below as Comparative Examples.

Comparative Example 1

A contact lens composed of 45 weight mol % of methacryloxyethoxypropyltris(trimethyl siloxy) silane, 20 weight mol % of hexafluoroisopropyl methacrylate, 20 weight mol % of methyl methacrylate, 8 weight mol % of methacrylic acid and 7 weight mol % of triethylene glycol dimethacrylate was prepared.

Comparative Example 2

A contact lens composed of 98.2 weight mol % of n-butyl acrylate and 1.8 weight mol % of ethylene glycol dimethacrylate was prepared.

Comparative Example 3

A contact lens composed of 74 weight mol % of vinyl pyrrolidone, 25 weight mol % of methl methacrylate and 1 weight mol % of diallylitaconate was prepared.

Characteristic properties of each of the contact lenses prepared in Examples 1 to 4 and Comparative Examples 1 to 3 were examined. In the examination, the amount of proteins adhered on the surface of the contact lens was obtained by analyzing a quantity of the remaining proteins after dipping in a protein solution of 2 ppm concentration for 24 hours at 37° C. Biocompatibilities were evaluated by the amount of proteins adhered on the surface of the contact lens. The less amount of proteins adhered, the better biocompatibilities the lens had, and the results are shown in Table 1. In the column "Adhesion of proteins" of Table 1, the evaluation marks denote as follows.

Amount of protein adhered

⊚: less than 0.5 $\mu$g

○: 1.0 $\mu$g or more~less than 0.5 $\mu$g

Δ: 0.5 $\mu$g or more~less than 1.0 $\mu$g

X: 1.0 $\mu$g or more

The easiness of washing out the proteins was rated by the method shown below. After immersing a contact lens in a protein solution of 20 ppm concentration for 24 hours at 37° C., it was washed with a prescribed quantity of saline water to obtain a contact lens which had proteins adhered on its surface. Then, the contact lens obtained was immersed in an aqueous solution of sodium sulfate of 0.8 weight % concentration for 24 hrs at 40° C. to wash out proteins adhered. Thereafter, the contact lens was taken out and rinsed with a 0.8% sodium sulfate solution. The easiness of washing out the proteins was evaluated by the quantity of proteins existing in the 0.8% sodium sulfate solutions in which the lens was immersed and rinsed. The more quantity of proteins is found in the solutions in which the lens was immersed and rinsed, the better performance of easiness of washing out the proteins is shown, and the amount of proteins found in the solutions is shown as follows.

Amount of proteins removed

⊚: 1.5 $\mu$g or more

○: 1.0 $\mu$g or more~less than 1.5 $\mu$g

Δ: 0.5 $\mu$g or more~less than 1.0 $\mu$g

X : less than 0.5 $\mu$g

The results are shown in Table 1.

TABLE 1

|  | Adhesion of proteins | Easiness of washing out of proteins |
|---|---|---|
| Example-1 | ⊚ | ⊚ |
| Example-2 | ○ | ⊚ |
| Example-3 | ⊚ | ⊚ |

TABLE 1-continued

|  | Adhesion of proteins | Easiness of washing out of proteins |
|---|---|---|
| Example-4 | ○ | ○ |
| Comp. Example-1 | ○ | Δ |
| Comp. Example-2 | X | X |
| Comp. Example-3 | X | X |

Com. Example = Comparative Example

These results show that in the contact lenses from biocompatible lens of the present invention, adhesion of proteins to lens is well inhibited and proteins adhered are easily washed out.

From the results above mentioned, it has become clear that biocompatible lenses inhibit adhesion of proteins, lipid and the like and the proteins and lipid adhered are easily washed out.

EXAMPLE 5

In this Example, biocompatibilities of the lens in this invention with a tissue were evaluated. Contact lenses obtained in Example-1 and Comparative Example-1 were implanted in the subcutaneous tissue of the back of rats, and taken out after a month. The tissue around the lens was investigated, and it was found that the lens obtained in Example-1 caused less inflammation reaction and less sticking to the tissue in comparison of the lens obtained in the Comparative Example 1. It is apparent from these results that the materials used in Example-1 can be advantageously used not only for a contact lens directly contacted to eyeball but also for an artificial crystalline lens.

Further, though in Examples 1 to 3, materials which inhibit adhesion of proteins or the like and from which proteins adhered are easily washed out were graft-polymerized onto the surface of the lens and in example 4, materials which show the same effect as in Examples 1 to 3 are coated and then made insoluble through cross-linking by heat treatment, it is not always necessary to subject the material to graft-polymerization or cross-linking. It is enough only to coat the surface of the lens with the materials that show the same effect as in Example 1 to 4, dissolved in an organic solvent, and then to remove the solvent.

As detailedly described above, a biocompatible lens provided by the present invention is almost free from adhesion of proteins, lipid and the like and even if they adhere on its surface, it is ease to wash out them. The biocompatible lens is suitable for use as an artificial crystalline lens because it has biocompatible surface. According to the method of this invention, it is possible to produce simply and easily the biocompatible lens which inhibits adhesion of proteins, lipid and the like.

What I claim is:

1. A biocompatible lens used for a contact lens directly contacted to the eyeball via tears or for an artificial crystalline lens, wherein alkoxyalkyl (meth)acrylate (co)polymer layer is formed on the surface of the lens.

2. The biocompatible lens according to claim 1, wherein the alkoxyalkyl (meth)acrylate (co)polymer layer is formed on the surface of the above lens by graft-polymerization or by coating.

3. The biocompatible lens according to claim 1, wherein the alkoxyalkyl (meth)acrylate is methoxyalkyl (meth)acrylate or ethoxyalkyl (meth)acrylate.

4. The biocompatible lens according to claim 1, wherein the alkoxyalkyl (meth)acrylate (co)polymer is a (co)polymer containing at least one kind selected from the group consisting of poly-2-methoxyethyl acrylate, poly-2-methoxyethyl methacrylate, poly-2-ethoxyethyl acrylate and poly-2-ethoxyethyl methacrylate.

5. A process for the production of a biocompatible lens, comprising the steps of:

generating radical species on the surface of the lens;

coating the surface of the above lens with monomers which at least contain alkoxyalkyl (meth)acrylate; and polymerizing the above monomers on the surface of the above lens with the above radical species generated as an initiator on the surface of the lens.

6. A process for the production of a biocompatible lens, comprising the steps of:

diluting an alkoxyalkyl (meth)acrylate (co)polymer with a solvent;

coating the surface of the lens with the above alkoxyalkyl (meth)acrylate (co)polymer solution; and removing, on the surface of the above lens, the solvent used for solving the above alkoxyalkyl (meth)acrylate (co)polymer.

\* \* \* \* \*